United States Patent [19]
Rauleder et al.

[11] Patent Number: 5,698,726
[45] Date of Patent: Dec. 16, 1997

[54] PROCESS FOR PREPARING AMINO-FUNCTIONAL ORGANOSILANES LOW IN OR FREE OF CHLORO-FUNCTIONAL ORGANOSILANES

[75] Inventors: Hartwig Rauleder; Claus-Dietrich Seiler; Hans-Joachim Koetzsch, all of Rheinfelden; Hans-Guenther Srebny, Duelmen, all of Germany

[73] Assignee: Huels Aktiengesellschaft, Marl, Germany

[21] Appl. No.: 642,336

[22] Filed: May 3, 1996

[30] Foreign Application Priority Data

May 4, 1995 [DE] Germany ............... 195 16 386.9

[51] Int. Cl.$^6$ ............... C07F 7/10; C07F 7/18
[52] U.S. Cl. ............... 556/413
[58] Field of Search ............... 556/413

[56] References Cited

U.S. PATENT DOCUMENTS

| | | | |
|---|---|---|---|
| 5,001,246 | 3/1991 | Ishimura et al. | 556/413 |
| 5,117,024 | 5/1992 | Dinh et al. | 556/413 |
| 5,210,254 | 5/1993 | Ritscher et al. | |

FOREIGN PATENT DOCUMENTS

| | | |
|---|---|---|
| 0 464 819 | 1/1992 | European Pat. Off. . |
| 0 595 488 | 5/1994 | European Pat. Off. . |
| 0 532 872 | 5/1995 | European Pat. Off. . |
| 0 702 017 | 3/1996 | European Pat. Off. . |
| 25 21 399 | 11/1976 | Germany . |
| 27 49 316 | 8/1978 | Germany . |
| 41 30 643 | 3/1993 | Germany . |
| 195 13 976 | 3/1996 | Germany . |

*Primary Examiner*—Paul F. Shaver
*Attorney, Agent, or Firm*—Oblon, Spivak, McClelland, Maier & Neustadt, P.C.

[57] ABSTRACT

The invention relates to a process for preparing amino-functional organosilanes which are low in chlorofunctional organosilanes or essentially free of chlorofunctional organosilanes, by reacting chloro-functional organosilanes with organic amines or ammonia and separating off the organic ammonium chlorides and/or the ammonium chloride thus formed, wherein the small amounts of chloro-functional organosilanes which have not reacted with ammonia or alkylamines are reacted by addition of at least one metal alkoxide in a reaction downstream of the aminosilane synthesis.

15 Claims, No Drawings

PROCESS FOR PREPARING AMINO-FUNCTIONAL ORGANOSILANES LOW IN OR FREE OF CHLORO-FUNCTIONAL ORGANOSILANES

BACKGROUND OF THE INVENTION

1. Field of the Invention

The invention relates to a process for preparing amino-functional organosilanes which are low in chloro-functional organosilanes or are essentially or completely free of chloro-functional organosilanes, comprising reacting chloro-functional organosilanes with organic amines or ammonia and separating off the organic ammonium chlorides and/or the ammonium chloride formed. The amino-functional organosilanes are hereinafter also referred to as aminosilanes.

2. Discussion of the Background

Amino-functional organosilanes are used, inter alia, in foundry technology as processing aids. They are also used, for example, as coupling agents for inorganic fillers in storage-stable resins or for glass fiber sizes.

Amino-functional organosilanes are generally prepared by reacting a chloro-functional organosilane with ammonia or an alkylamine at elevated temperatures under pressure, with the stoichiometric ratio of ammonia to chloro-functional organosilane being selected in such a way that the primary amine compound is preferentially formed. This occurs, for example, when using a more than 50-fold excess of ammonia, based on the amount of chloro-functional organosilane used. This amination process is carried out on a large scale in steel autoclaves which, owing to the high pressure intrinsic to the process, are complicated to construct and also represent a significant cost factor. The space-time yields achievable in such autoclaves are therefore to be viewed in terms of the amount of starting materials, their ratio to one another, the reaction pressure, the reaction temperature and the reaction time. The reaction time here has to be such that the reaction of the chloro-functional organosilane proceeds virtually to completion and the product quality achieved is as high as possible. Studies show that under the usual process conditions with respect to reaction pressure, the amount of starting materials and the reaction temperature, the degree of conversion of the chloro-functional organosilane is about 99.6% after only about 5 hours, but completion of the reaction requires the same time again as for reaching the conversion of 99.6%.

In the distillative work-up of the crude aminosilane product, which, despite the long time spent in the amination reaction, still contains appreciable residues of chloro-functional organosilane, it is found that distillative separation of the unreacted chlorofunctional organosilane from the target product is not possible with an economically justifiable effort, and this (the unreacted material) is still found as an impurity in the distillate, i.e. in the product.

In the amino-functional organosilanes being considered, the content of compounds containing non-hydrolyzable chlorine plays an important role in their usability, e.g. as coupling agent in glass fibre sizes, etc. The content of compounds containing non-hydrolyzable chlorine can be tolerated in the aminosilane products being discussed here only in the region of a few ppm by weight. For the purposes of the present invention compounds containing non-hydrolyzable chlorine are chloro-functional organosilanes, i.e. chloroorganosilanes. In contrast thereto, hydrolyzable chlorides are compounds such as organochlorosilanes, e.g. alkylchlorosilanes or the hydrochlorides of aminoalkylalkoxysilanes, i.e. amine hydrochlorides or alkylammonium chlorides or organic ammonium chlorides or organic hydrochlorides.

It has been found that aminosilane distillates which are free of hydrolyzable chloride immediately after completion of the distillation, but contain residues of unreacted chloro-functional organosilane, in the course of time develop a steadily increasing content of hydrolyzable chloride which is caused by gradual quaternization of the aminosilanes by residual amounts of chloro-functional organosilane and, depending on the amount of this present in the aminosilane, leads to the product becoming unusable in a relatively short period of time.

In German Patent Application No. 195 13 976.3, the preparation of low-chloride or chloride-free amino-functional organosilanes is described. According to that application, undesired amounts of chloride, caused by organic hydrochlorides such as aminoalkyl hydrochlorides, or ammonium chloride, i.e. hydrolyzable chlorides, can be virtually completely removed by reaction with metal alkoxides and separation of the metal chlorides thus formed from the aminosilane. However, the particular aspects of the production scale and the unreacted chloro-functional organosilanes present in the crude product of the aminosilane synthesis are here not taken into account.

OBJECTS OF THE INVENTION

It is therefore an object of the invention to provide a process which makes possible the large-scale preparation of amino-functional organosilanes low in or free of chloro-functional organosilanes.

DETAILED DESCRIPTION OF THE INVENTION

The above object is provided by a method for preparing amino-functional organosilanes which are low in chloro-functional organosilanes or are essentially free of chloro-functional organosilanes, which may be carried out on a large scale, and which is characterized in that the amounts of chloro-functional organosilane which have not reacted with ammonia or alkylamines are reacted by addition of metal alkoxides in a reaction downstream of the aminosilane synthesis. For the purposes of the present invention, amino-functional organosilanes which are low in chlorofunctional organosilanes or are essentially free of chloro-functional organosilanes are those products whose content of organically bound chlorine, i.e. chlorine from non-hydrolyzable chlorine compounds, is less than or equal to 30 ppm by weight, preferably less than or equal to 20 ppm by weight, including 15, 10, 5 and 0 ppm and all values and subranges between these several limits.

In the process of the invention, amino-functional organosilanes of the formula

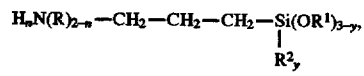

where R is a linear or branched alkyl radical having 1 to 3 carbon atoms and n is equal to 0 or 1 or 2, $R^1$ is a linear or branched alkyl radical having from 1 to 4 carbon atoms and $R^2$ is a methyl or phenyl radical and y is equal to 0 or 1 or 2, can generally be prepared.

Usually, in the process of the invention, chloroorganosilane compounds of the formula

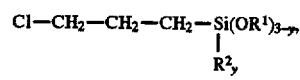

where $R^1$ is a linear or branched alkyl radical having from 1 to 4 carbon atoms and $R^2$ is a methyl or phenyl radical and y is equal to 0 or 1 or 2, are reacted with amines of the formula

where R is a linear or branched alkyl radical having 1 to 3 carbon atoms and m is equal to 1 or 2 or 3.

After separating off the ammonium/alkylammonium chloride formed, for example in the manner described in German Patent Application No. 195 13 976.3, the small amounts of unreacted chloro-functional organosilanes still present in the crude aminosilane can be treated with at least one metal alkoxide and the product mixture can be worked up using art accepted procedures selected from washing, filtering, separating, extracting, etc. The product mixture is usefully worked up by distillation.

The process of the invention is preferably used for preparing the following organosilanes:

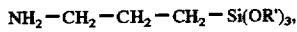

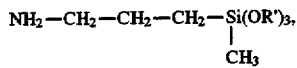

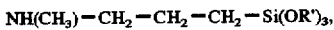

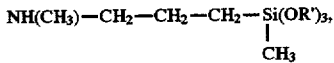

where R' is a $CH_3$ or $C_2H_5$ group.

In the process of the invention, preference is given to using metal alkoxides from the group of alkali metal and/or alkaline earth metal alkoxides, preferably at least one alkoxide. However, it is also possible to use alkoxides of other metals if desired. The particularly preferred alkoxide is that of sodium.

In particular, the metal alkoxides are preferably used in dissolved form, with the metal alkoxide preferably being added dissolved in alcohols. The alcoholic component of the alkoxide can also usefully be identical with the alkoxy groups located on the silicon atom of the aminofunctional organosilane. Likewise, the solvent alcohol used for the metal alkoxide can be that alcohol from which the alkoxy group of the metal alkoxide is derived.

In the process of the invention, the alkoxides are preferably added in amounts which are up to 10 times the molar amount of chloro-functional organosilane. It is also possible to use larger excesses of metal alkoxide.

The reaction for lowering or eliminating the chlorine present in the unreacted chloro-functional organosilane is advantageously carried out by adding a multiple (depending on the chloro-functional organosilane compound to be reacted) of the stoichiometric amount required for complete elimination of the chlorine present in the chloro-functional organosilane and reacting the mixture. It has been found to be particularly useful in practice to add an amount of metal alkoxide which corresponds to from 3 to 5 times the stoichiometrically required amount of metal alkoxide.

Preferably, the metal alkoxides are added to the crude aminosilane being worked up by distillation and the reaction is allowed to proceed during the course of the distillative work-up. Depending on the method of distillation used, batchwise or continuous, and depending on the operating pressure, e.g., in the plant, the metal alkoxide/chlorofunctional organosilane/amino-functional organosilane system generally passes through the temperature range from 20° C. up to 200° C. In operational practice, the system to be distilled is preferably kept in the temperature range from 80° C. to 160° C., particular preference being given to the temperature range from 100° C. to 130° C.

For the reaction of the chlorine-containing substrate with at least one metal alkoxide, it has been found to be extremely advantageous to carry this reaction out with vigorous stirring, which leads to complete reaction of the reactants in a short time. The reaction can be carried out at reduced pressure, atmospheric pressure or at elevated pressure.

By means of the process of the invention, aminofunctional organosilanes which are low in chlorofunctional organosilanes or are essentially free of chloro-functional organosilanes can now be prepared on a large scale.

Furthermore, a particularly economical advantage is achieved in the process of the invention: the actual amination time necessary for maximum conversion in the aminosilane synthesis can be significantly reduced by means of the invention, i.e. a very low residual content of unreacted chloro-functional organosilane in the crude aminosilane can be achieved by the measures of the invention rather than by a long reaction time. The process of the invention can thus contribute to a significant capacity increase even in an existing production plant.

The invention will now be further illustrated by the following non-limiting examples:

EXAMPLES

Comparative Example A 1000 g of 3-aminopropyltriethoxysilane having a content of hydrolyzable chloride of less than 2 ppm by weight and a content of total chlorine of less than 30 ppm by weight are admixed with 2 g of 3-chloropropyltriethoxysilane. The determination of the total chlorine content of the mixture gives a value of 320 ppm by weight.

After standing for 3 months, the content of hydrolyzable chloride in the mixture is determined. A value of 187 ppm by weight is found.

Comparative Example B

In an autoclave, 4830 g (20 mol) of 3-chloropropyltriethoxysilane are reacted with 17 kg (1000 mol) of ammonia at 70° C. for a period of 13 hours. To reduce the amount of ammonium chloride dissolved in the organosilane, the contents of the autoclave were admixed while stirring at room temperature with hexane. The salt was separated off by filtration. The filtrate obtained was freed of hexane by distillation under reduced pressure. Such methodology is also explained in U.S. Ser. No. 08/527,873, incorporated herein by reference. The crude aminosilane obtained is worked up by distillation.

A content of total chlorine of less than 30 ppm by weight is found in the distillate, the content of hydrolyzable chloride is below 2 ppm by weight.

After standing for 3 months, the content of hydrolyzable chloride is again determined. A value of 3 ppm by weight is found.

Comparative Example C

In an autoclave, the reaction of Comparative Example B is repeated, but the reaction time is reduced from 13 to 8 hours. The autoclave product is worked up as described in Comparative Example B and the content of total chloride in the distillate is found to be 310 ppm by weight, the content of hydrolyzable chloride is determined as 3 ppm by weight.

After the distillate has stood for 3 months, the content of hydrolyzable chloride is again determined. A value of 152 ppm by weight is found.

Comparative Example D

In an autoclave, the reaction of Comparative Example B is repeated, but the reaction time is reduced from 13 hours to 5 hours.

The autoclave product is worked up as described and the content of total chlorine in the distillate is found to be 620 ppm by weight, the content of hydrolyzable chloride is less than 2 ppm by weight. After the distillate has stood for 3 months, the content of hydrolyzable chloride is again determined. A value of 210 ppm by weight is found.

Example 1

In an autoclave, the reaction of Comparative Example D is repeated. To reduce the amount of ammonium chloride dissolved in the organosilane, the contents of the autoclave were admixed while stirring at room temperature with hexane. The salt was separated off by filtration. The filtrate obtained was freed of hexane by distillation under reduced pressure. Such methodology is described in U.S. Ser. No. 08/527,873 incorporated herein by reference. The contents of total chlorine and hydrolyzable chloride are determined in the product to be distilled. The content of total chlorine is determined as 590 ppm by weight, that of hydrolyzable chloride as less than 1 ppm by weight.

To the measured proportion used for the distillation there is added an amount of 20% strength ethanolic sodium ethoxide solution corresponding to 5 times the total chlorine amount of 590 ppm by weight.

Distillation is carried out with intense stirring. The content of total chlorine and hydrolyzable chloride in the distillate obtained is determined. The total chlorine content is determined as less than 30 ppm by weight, the content of hydrolyzable chloride as less than 1 ppm by weight.

After the distillate has stood for 3 months, the content of hydrolyzable chloride is again determined. The value of less than 1 ppm by weight which was found in the fresh distillate is confirmed.

Accordingly, the invention provides storage stable products wherein the content of hydrolyzable chloride remains relatively constant even after standing at room temperature for 3 months. By "relatively constant" it is meant that the amount of hydrolyzable chloride in the product increases less than 10%, preferably less than 5%, most preferably less than 3% including 1%, 2% and 0%.

What is claimed as new and is desired to be secured by Letters Patent of the United States is:

1. A process for preparing amino-functional organosilanes which are low in chloro-functional organosilanes or are essentially free of chloro-functional organosilanes, comprising the steps of reacting chloro-functional organosilanes with organic amines or ammonia and separating off the organic ammonium chlorides and/or the ammonium chloride formed, wherein residual chloro-functional organosilanes which have not reacted with the ammonia or organic amines are reacted by addition of at least one metal alkoxide to the amino-silane synthesis products in a reaction downstream of the aminosilane synthesis.

2. The process according to claim 1, wherein at least one metal alkoxide is added to the amino-silane synthesis products containing chlorofunctional organosilanes in an amount which is up to 10 times the residual molar amount of chloro-functional organosilane.

3. The process according to claim 2, wherein at least one metal alkoxide is added in an amount which corresponds stoichiometrically to up to 5 times the amount of the chloro-functional organosilane, based on the residual molar amount of the latter in the aminosilane synthesis product.

4. The process according to claim 1, wherein the reaction of the residual amount of chloro-functional organosilanes with at least one metal alkoxide is carried out at a temperature of from 20° C. to 200° C.

5. The process according to claim 1, wherein the reaction of the residual amount of chloro-functional organosilanes with the at least one metal alkoxide is carried out under reduced pressure.

6. The process according to claim 1, wherein the reaction of the residual amount of chloro-functional organosilanes with said at least one metal alkoxide is carried out with stirring.

7. The process according to claim 1, wherein the metal alkoxide is at least one alkoxide of an alkali metal and/or an alkaline earth metal.

8. The process according to claim 1, wherein the metal alkoxide is in dissolved form.

9. The process according to claim 1, wherein at least one metal alkoxide is dissolved in an alcohol or an alcohol mixture.

10. The process according to claim 9, wherein the solvent used for the metal alkoxide is the alcohol corresponding to the respective alkoxide.

11. The process according to claim 1, wherein the reaction of the residual amount of chloro-functional organosilanes with the at least one metal alkoxide is carried out under elevated pressure.

12. The process according to claim 1, wherein the reaction of the residual amount of chloro-functional organosilanes with the at least one metal alkoxide is carried out under atmospheric pressure.

13. The process according to claim 1, wherein said chloro-functional organosilanes are of the formula

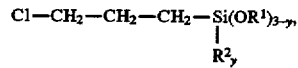

where $R^1$ is a linear or branched alkyl radical having from 1 to 4 carbon atoms and $R^2$ is a methyl or phenyl radical and y is equal to 0 or 1 or 2.

14. The process according to claim 1, wherein said amino-functional organosilanes are of the formula

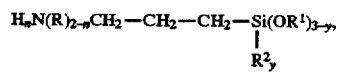

where R is a linear or branched alkyl radical having 1 to 3 carbon atoms and n is equal to 0 or 1 or 2, $R^1$ is a linear or branched alkyl radical having from 1 to 4 carbon atoms and $R^2$ is a methyl or phenyl radical and y is equal to 0 or 1 or 2.

15. The process according to claim 13, wherein said organic amines or ammonia are of the formula

where R is a linear or branched alkyl radial having 1 to 3 carbon atoms m is equal to 1 or 2 or 3.

* * * * *